(12) United States Patent
McMillan

(10) Patent No.: US 6,534,645 B2
(45) Date of Patent: Mar. 18, 2003

(54) COMPOSITIONS AND METHODS ENABLING A TOTALLY INTERNALLY CONTROLLED AMPLIFICATION REACTION

(75) Inventor: William A. McMillan, Cupertino, CA (US)

(73) Assignee: Cepheid, Sunnyvale, CA (US)

( * ) Notice: Subject to any disclaimer, the term of this patent is extended or adjusted under 35 U.S.C. 154(b) by 0 days.

(21) Appl. No.: 09/925,123

(22) Filed: Aug. 8, 2001

(65) Prior Publication Data

US 2002/0119464 A1 Aug. 29, 2002

Related U.S. Application Data

(62) Division of application No. 09/747,875, filed on Dec. 22, 2000, now Pat. No. 6,312,929.

(51) Int. Cl.$^7$ .......................... C07H 21/04; C12Q 1/68; C12P 19/34

(52) U.S. Cl. ..................... 536/24.3; 536/23.1; 536/23.5; 536/24.32; 536/24.33; 435/6; 435/91.1; 435/91.2; 435/810

(58) Field of Search ........................... 536/24.33, 24.32, 536/24.3, 23.1; 435/6, 91.1, 91.2, 810

(56) References Cited

U.S. PATENT DOCUMENTS

| | | | | | |
|---|---|---|---|---|---|
| 5,705,627 | A | * | 1/1998 | Manos et al. | 536/24.3 |
| 5,952,202 | A | * | 9/1999 | Aoyagi et al. | 435/91.2 |
| 6,174,670 | B1 | * | 1/2001 | Wittwer et al. | 435/6 |
| 6,268,148 | B1 | * | 7/2001 | Barany et al. | 435/6 |

* cited by examiner

Primary Examiner—Kenneth R. Horlick
Assistant Examiner—Alexander H. Spiegler
(74) Attorney, Agent, or Firm—Townsend and Townsend and Crew LLP

(57) ABSTRACT

The present invention provides compositions and methods for performing an amplification reaction of nucleic acids with internal controls that test the integrity of all aspects of the amplification reaction.

5 Claims, 1 Drawing Sheet

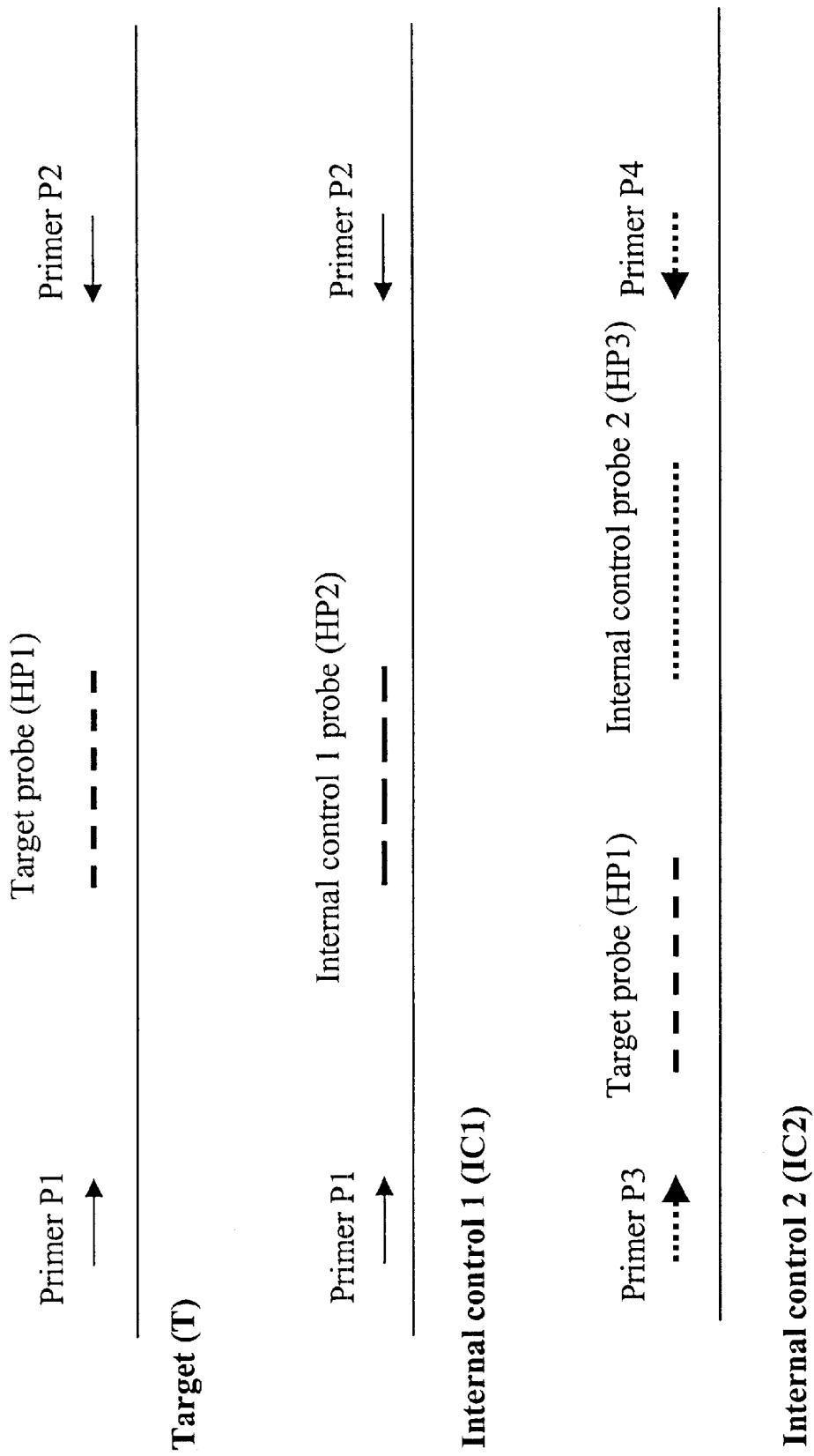

COMPOSITIONS AND METHODS ENABLING A TOTALLY INTERNALLY CONTROLLED AMPLIFICATION REACTION

CROSS-REFERENCE TO RELATED APPLICATION

The present application is a divisional application of U.S. application Ser. No. 09/747,875 filed Dec. 22, 2000, now U.S. Pat. No. 6,312,929.

BACKGROUND OF THE INVENTION

Methods for amplifying nucleic acids provide useful tools for the detection of human pathogens, detection of human genetic polymorphisms, detection of RNA and DNA sequences, for molecular cloning, sequencing of nucleic acids, and the like. In particular, the polymerase chain reaction (PCR) has become an important tool in the cloning of DNA sequences, forensics, paternity testing, pathogen identification, disease diagnosis, and other useful methods where the amplification of a nucleic acid sequence is desired. See e.g., *PCR Technology: Principles and Applications for DNA Amplification* (Erlich, ed., 1992); *PCR Protocols: A Guide to Methods and Applications* (Innis et al., eds, 1990).

PCR permits the copying, and resulting amplification, of a target nucleic acid. Briefly, a target nucleic acid, e.g. DNA, is combined with a sense and antisense primers, dNTPs, DNA polymerase and other reaction components. See Innis et al. The sense primer can anneal to the antisense strand of a DNA sequence of interest. The antisense primer can anneal to the sense strand of the DNA sequence, downstream of the location where the sense primer anneals to the DNA target. In the first round of amplification, the DNA polymerase extends the antisense and sense primers that are annealed to the target nucleic acid. The first strands are synthesized as long strands of indiscriminate length. In the second round of amplification, the antisense and sense primers anneal to the parent target nucleic acid and to the complementary sequences on the long strands. The DNA polymerase then extends the annealed primers to form strands of discrete length that are complementary to each other. The subsequent rounds serve to predominantly amplify the DNA molecules of the discrete length.

A variety of factors can lead to non-functional PCR or other amplification reactions. One drawback of PCR is that artifacts can be generated from mis-priming and primer dimerization. Those artifacts can be exacerbated in traditional multiplex PCR. Multiple sets of primers increase the possibility of primer complementarity at the 3'-ends, leading to primer-dimer formation. These artifacts deplete the reaction of dNTPs and primers and outcompete the multiplex templates for DNA polymerase. Such artifacts can be reduced by careful primer design and the use of "hot start" PCR. See Chou, Q. et al. (1992) *Nucleic Acids Research*, 20: 1717-1723. It is increasingly difficult, however, to eliminate all interactions which promote the mis-priming and primer dimerization in a multiplex amplification as the reaction may contain many primers at high concentration.

Additionally, multiplex PCR has been observed to suppress the amplification of one template in preference for another template. A number of factors are involved in this suppression. For example, when a multiplex PCR reaction involves different priming events for different target sequences, the relative efficiency of these events may vary for different targets. This can be due to the differences in thermodynamic structure, stability, and hybridization kinetics among the various primers used.

Simple user error, of course, can also result in a nonfunctional amplification reaction. For instance, the absence of nucleotides or enzyme due to negligence or degradation will lead to a nonfunctional reaction. Similarly, where probes are used to monitor a particular reaction, a nonfunctional probe will lead to a false negative reaction. This can occur, for instance, when there is an absence of probe or the probe does not bind to its hybridization site efficiently. Use of probes, particularly fluorescent probes, are commonly used for monitoring the accumulation of reaction products in real time, i.e. while that amplification reaction is progressing.

Several schemes for controlling for failure of an amplification reaction have been described. See, e.g., Edwards, M., et al. PCR PRIMER, A LABORATORY MANUAL (Dieffenbach, C., et al., eds. 1995) pages 157-171. For example, it is common to run positive and negative control reactions in separate reaction tubes. Simple positive controls include a known amount of template, while negative controls do not have any template in the reaction. These controls are run under the same conditions as a test sample and provide the tester with information about the quality of the enzymes and nucleotides, etc., as well as whether the test solutions are contaminated.

More recently, internal controls for PCR have been developed. Internal controls are advantageous because they are run in the exact same reaction mixture as the test sample and therefore there is no question about the activity of the reagents in the test sample itself. Moreover, internal controls are more efficient by allowing for the use of fewer reactions and less reaction solution and reagents.

Internal controls typically involve multiple reactions performed in the same reaction tube (e.g., multiplex PCR). In such reactions, the presence of at least one amplification product indicates that some variables, such as the enzyme and nucleotides, were functional during the reaction. See, e.g. Levinson, G. et al. *Human Reprod.* 7(9):1304-1313 (1992).

In addition, internal controls to verify the presence of the target template have also been described. For example, in multiplex assays where closely related templates such as pathogen strains are distinguished by amplifying differing sequences, primers for a sequence common to all templates provides a positive control for amplification. See, e.g., Kaltenboeck, B., et al. *J. Clin. Microbiol.* 30(5):1098-1104 (1992); Way, J., et al. *App. Environ. Microbiol.* 59(5):1473-1479 (1993); Wilton, S. et al. *PCR Methods Appl.* 1:269-273 (1992). Rosenstraus et al. (*J. Clin. Microbiol.* 36(1):191-197 (1998)) have described an internal control containing primer binding regions identical to those of the target sequence and that contain a unique probe-binding region that differentiates the control from the amplified target sequence.

As discussed above, it is often desirable to quantify PCR products using various fluorescent probes. Examples of useful fluorescent probes include, e.g., fluorescence resonance energy transfer (FRET), molecular beacon, and Taq-Man® probes. Currently, however, there is no internal control method that validates the activity of a target specific probe in the same reaction mixture as the test sample. Therefore, to have a fully validated amplification reaction, a positive control must be run in a separate reaction tube to insure that the target specific probe is functioning properly.

Accordingly, there is a need for internal control compositions and methods useful for measuring these and other amplification variables. The present invention meets this need and provides useful methods and compositions for performing a totally internally controlled amplification reaction.

SUMMARY OF THE INVENTION

The present invention provides methods of performing an amplification reaction. The steps of the reaction comprise:

(a) combining in an aqueous solution,
  (i) a target probe, a first control probe and a second control probe;
  (ii) a first 5' primer, a first 3' primer and a target template, the target template comprising a hybridization site for the first 5' primer, the first 3' primer and the target probe;
  (iii) a first control template, the first control template comprising a hybridization site for the first 5' primer, the first 3' primer and the first control probe; and
  (iv) a second 5' primer, a second 3' primer and a second control template, the second control template comprising a hybridization site for the second 5' primer, the second 3' primer, the target probe and a second control probe;
(b) performing an amplification reaction; and
(c) quantifying binding of the target probe, first control probe and second control probe.

In some embodiments, the quantifying step is performed during the amplification reaction. In some embodiments, the quantifying step is performed after the amplification reaction.

In some embodiments, the target probe, first control probe and second control probe comprise a fluorophore. For example, the target probe, first control probe and second control probe can each comprise a fluorophore which fluoresces at a different wavelength of light. In some embodiments, the target probe, first control probe and second control probe further comprise a quenching reagent. In some embodiments, the target probe, first control probe and the second control probe are enzymatically cleaved during the amplification reaction. For instance, the quenching reagent and the fluorophore can be separated when the probes hybridize to their hybridization sites.

In some embodiments, the amplification reaction is a thermocyclic amplification reaction. For example, the thermocyclic amplification reaction can be a polymerase chain reaction (PCR). In some embodiments, the amplification reaction is an isothermal reaction. For example, the isothermal reaction can be a transcription-mediated amplification (TMA).

The present invention also provides kits comprising:
(a) a target probe, a first control probe and a second control probe;
(b) a first 5' primer and a first 3' primer;
(c) a first control template, the first control template comprising a hybridization site for the first 5' primer, the first 3' primer and the first control probe; and
(d) a second 5' primer, a second 3' primer and a second control template, the second control template comprising a hybridization site for the second 5' primer, the second 3' primer, the target probe and the second control probe.

In some embodiments, the kit further comprises nucleotides and a DNA polymerase. In some embodiments, the target probe, first control probe and second control probe comprise a fluorophore. For example, the target probe, first control probe and second control probe can further comprise a quenching reagent.

The present invention also provides a solution comprising:
(a) a target probe, a first control probe and a second control probe;
(b) a first 5' primer and a first 3' primer;
(c) a first control template, the first control template comprising a hybridization site for the first 5' primer, the first 3' primer and the first control probe; and
(d) a second 5' primer, a second 3' primer and a second control template, the second control template comprising a hybridization site for the second 5' primer, the second 3' primer, the target probe and the second control probe.

In some embodiments, the solution further comprises nucleotides and a DNA polymerase. Moreover, the target probe, first control probe and second control probe can comprise a fluorophore. In addition, the target probe, first control probe and second control probe further comprise a quenching reagent.

DEFINITIONS

An "amplification reaction" refers to any chemical, including enzymatic, reaction that results in increased copies of a template nucleic acid sequence. Amplification reactions include polymerase chain reaction (PCR) and ligase chain reaction (LCR) (see U.S. Pat. Nos. 4,683,195 and 4,683,202; *PCR Protocols: A Guide to Methods and Applications* (Innis et al., eds, 1990)), strand displacement amplification (SDA) (Walker, et al. *Nucleic Acids Res.* 20(7):1691-6 (1992); Walker *PCR Methods Appl* 3(1):1-6 (1993)), transcription-mediated amplification (Phyffer, et al., *J. Clin. Microbiol.* 34:834-841 (1996); Yuorinen, et al., *J. Clin. Microbiol.* 33:1856-1859 (1995)), nucleic acid sequence-based amplification (NASBA) (Compton, *Nature* 350(6313):91-2 (1991), rolling circle amplification (RCA) (Lisby, *Mol. Biotechnol.* 12(1):75-99 (1999)); Hatch et al., *Genet. Anal.* 15(2):35-40 (1999)) and branched DNA signal amplification (bDNA) (see, e.g., Iqbal et al., *Mol. Cell Probes* 13(4):315-320 (1999)).

A "thermocyclic amplification reaction" refers to the amplification of DNA fragments by using primer oligonucleotides which, with the aid of a thermostable enzyme, synthesizes or ligates copies a template nucleic acid sequence. Thermocyclic reactions such as the polymerase chain reaction (PCR) and the ligase chain reaction (LCR) are well known.

A "target" or "target nucleic acid" refers to a single or double stranded polynucleotide sequence sought to be amplified in a thermocyclic amplification reaction.

A "probe" refers to a polynucleotide sequence capable of hybridization to a polynucleotide sequence of interest and allows for the detecting of the polynucleotide sequence of choice. For example, "probes" can comprise polynucleotides linked to fluorescent or radioactive reagents, thereby allowing for the detection of these reagents.

A "template" refers to a double stranded polynucleotide sequence that comprises the polynucleotide to be amplified, flanked by primer hybridization sites. Thus, a "target template" comprises the target polynucleotide sequence flanked by hybridization sites for a 5' target primer and a 3' target primer. A "control template" refers to a polynucleotide sequence that is flanked by primer hybridization sequences.

A "5' target primer" refers to a polynucleotide sequence, typically less than 100 nucleotides in length, which hybridizes to a sequence on the target template that is upstream from the target polynucleotide. A "3' target primer" refers to a polynucleotide sequence, typically less than 100 nucleotides in length, whose complement hybridizes to a sequence on the target template downstream from the target polynucleotide.

A "hybridization site" refers to a polynucleotide sequence that is the complement for a primer or probe polynucleotide sequence and that can be bound by a specific primer or probe.

"Quantifying binding" refers to measuring the absolute or relative binding of probe molecules to regions of nucleic acid sequence to which they hybridize. For instance, binding of fluorescent probes using FRET technology can be measured by quantifying the amount of light emitted from a sample at a particular wavelength. Alternatively, binding of probes using standard blotting and hybridization techniques (e.g., Southern blotting) can be quantified with a variety of computer-based scanning devices.

"Substantially equal concentrations" means that the concentration of one solute is from 95% to 105% of the concentration of at least one other solute in a solution.

The term "fluorophore" refers to chemical compounds which, when excited by exposure to particular wavelengths of light, emit light (i.e. fluoresce) at a different wavelength. When the excited-state energy of the fluorophore is transferred to a non-fluorophore acceptor, the fluorescence of the fluorophore is quenched without subsequent emission of fluorescence by the acceptor. In this case, the acceptor functions as a "quenching agent".

The phrase "nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

The following abbreviations are provided for the reader's convenience:

Target=T

Internal control 1 (or first control template)=IC1

Internal control 2 (or second control template)=IC2

Forward (or first 5') primer for target and IC1=P1

Reverse (or first 3') primer for target and IC1=P2

Forward (or second 5') primer for IC2=P3

Reverse (or second 3' ) primer for IC2=P4

Hybridization probe for the target and IC2 ("target probe")=HP1

Hybridization probe for IC1 ("first control probe")=HP2

Hybridization probe for IC2 ("second control probe")=HP3

BRIEF DESCRIPTION OF THE DRAWINGS

FIG. 1 is a schematic representation of an embodiment of the invention. Primers P1 and P2 direct amplification of the target template. In this embodiment, there are three templates: the target template (T), the internal control 1 template (IC1) and the internal control 2 template (IC2). The product of this reaction is bound by the target probe (HP1). Primers 1 and 2 also direct amplification from internal control 1 template. The product of this reaction is bound by the internal control 1 probe (HP2). Finally, primers P3 and P4 direct amplification from the internal control 2 template. The product of this reaction can be bound by both HP1 and internal control 2 probe (HP3).

DESCRIPTION OF THE SPECIFIC EMBODIMENTS

I. Introduction

The present invention provides novel methods, kits and solutions that provide a complete internal control for amplification reactions such as PCR. In particular, the invention provides at least three polynucleotide sequences: a target template (T) and two control templates (IC1 and IC2). The two control templates function to control for the integrity of the amplification reaction. Amplification products of the target and of the control templates can be measured by quantifying probe binding to reaction products. Thus, each amplification product provides a target for at least one corresponding probe that is useful for detecting and quantifying the amplification products.

The invention provides a target template (T) that comprises a nucleic acid sequence with hybridization sites for a 5' and 3' target primer (P1 and P2, respectively). The target template (T) comprises a polynucleotide sequence that is sought to be amplified ("the target sequence"). This sequence, or a subsequence of this sequence, provides a hybridization sequence for a target probe (HP1).

The first control template (IC1) comprises the same target primer hybridization sequences (i.e., for P1 and P2) as the target template (T) and a probe hybridization sequence that is different from the target template. Thus, amplification of this template controls for the integrity of the general reaction, e.g., function of enzyme, reagents, target primers, etc. For example, if no target product is produced, but the first control template (IC1) is amplified in a reaction, this indicates that amplification conditions (buffer, temperature, primers, enzymes, etc.) were capable of amplifying a template. If the first control template (IC1) is not amplified, then it is likely that the reaction mixture was defective and therefore, a negative product from the template may not be due to lack of template.

The second control template (IC2) comprises hybridization sequences for the target probe (HP1) and a second control probe (HP3). These two sequences are flanked by hybridization sequences for a pair of second control primers (P3 and P4). Amplification of this template provides a control for binding of the target probe (HP1 ) to the target sequence. For example, if the second control probe (HP3) does not produce any signal, then it is likely that there was no amplification of the second control template (IC2). However, if the second control probe (HP3) produces signal but the target probe (HP1) does not, then it is likely that the target probe (HP1) has failed to function.

Because the second control template (IC2) has one copy each of the target probe hybridization sequence and the second control hybridization sequence, signal from the target probe (HP1) and the second control probe (HP3) should be substantially equal if the target template (T) is not present. If the target template (T) is present, then more target probe (HP1) hybridization sequences (i.e., target amplification products) should be available relative to second control probe (HP3) hybridization sequences. Thus, a properly functioning reaction should have higher signal from a target probe (HP1) than from the second control probe (HP3). This is particularly true in earlier amplification cycles. Therefore, in some embodiments, real time measurements of probe binding can be useful, e.g., for quantitative PCR, as discussed below.

II. Target Templates

Target nucleic acid sequences may be double or single-stranded DNA or RNA from any biological source, e.g., a bacterium, an animal, a plant, etc. Preferably, the target template is an isolated DNA sequence. Target DNA sequences may be isolated using a variety of techniques. For example, methods are known for lysing organisms and preparing extracts or purifying DNA. See, Current Protocols in Molecular Biology Volumes 1-3, John Wiley & Sons, Inc. (Ausubel et al., eds., 1994-1998) (hereinafter "Ausubel et al."). Also, total RNA or polyA+ RNA can be reverse transcribed to produce cDNA that can serve as the target DNA.

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual,* Cold Spring Harbor Laboratory, Cold Spring Harbor, N.Y., (1989) or Ausubel et al., supra.

In general, the nucleic acid sequences encoding genes of the target DNA sequences of interest are cloned from cDNA and genomic DNA libraries by hybridization with a probe, or isolated using amplification techniques with oligonucleotide primers. Preferably, target template sequences are polynucleotide sequences from human pathogens. In another embodiment, the target template is derived from mammalian (e.g., human) nucleic acids. Target DNA sequences are typically isolated from mammalian nucleic acid (genomic or cDNA) libraries by hybridizing with a nucleic acid probe, the sequence of which can be derived from the gene of the target DNA sequence being cloned.

Primer-based amplification techniques can also be used to amplify and isolate target DNA sequences from DNA or RNA (see, e.g. Dieffenfach & Dveksler, (1995) *PCR Primer: A Laboratory Manual*). Primers can be used, e.g., to amplify either the full length sequence or a probe of one to several hundred nucleotides, which is then used to screen a mammalian library for a full-length nucleic acid of choice. For example, degenerate primer sets, can be used to isolate relevant target DNA sequences. Nucleic acids can also be isolated from expression libraries using antibodies as probes. Such polyclonal or monoclonal antibodies can be raised using the predicted amino acid sequence of the target DNA sequence being cloned.

Polymorphic variants and alleles that are substantially identical to the target DNA sequence of choice can be isolated using nucleic acid probes, and oligonucleotides under stringent hybridization conditions, by screening libraries. Alternatively, expression libraries can be used to clone variants of the target DNA sequence being cloned such as, polymorphic variants, interspecies homologs, and alleles, by detecting expressed homologs immunologically with antisera or purified antibodies made against the predicated amino acid sequence of the target DNA sequence.

To make a cDNA library, one should choose a source that is rich in the mRNA of the target DNA sequence of interest. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, (1983) *Gene* 25:263-269; Sambrook et al., ($2^{nd}$ ed. 1989) *Molecular Cloning, A Laboratory Manual;* and Ausubel et al.

For a genomic library, the DNA is extracted from the tissue and either mechanically sheared or enzymatically digested to yield fragments of about 12-20 kb. The fragments are then separated by gradient centrifugation from undesired sizes and are constructed in non-lambda expression vectors. These vectors are packaged in vitro. Recombinant phage are analyzed by plaque hybridization as described in Benton & Davis, (1977) *Science* 196:180-182. Colony hybridization is carried out as generally described in Grunstein et al., (1975) *Proc. Natl. Acad. Sci. USA.,* 72:3961-3965. An alternative method of isolating a nucleic acid and its homologs combines the use of synthetic oligonucleotide primers and amplification of an RNA or DNA template using PCR (see below).

Synthetic oligonucleotides can be used to construct recombinant nucleic acids for use as probes or for expression of the target DNA sequence proteins. Oligonucleotides can be chemically synthesized according to the solid phase phosphoramidite triester method first described by Beaucage & Caruthers, (1981) *Tetrahedron Letts.* 22:1859-1862, using an automated synthesizer, as described in Van Devanter et al., (1984) *Nucleic Acids Res.* 12:6159-6168. Purification of oligonucleotides is typically performed by either native acrylamide gel electrophoresis or by anion-exchange HPLC as described in Pearson & Reanier, (1983) *J. Chrom.* 255:137-149. The sequence of the cloned genes and synthetic oligonucleotides can be verified after cloning using, e.g., the chain termination method for sequencing double-stranded templates of Wallace et al., (1981) *Gene* 16:21-26. This method is performed using a series of overlapping oligonucleotides usually 40-120 bp in length, representing both the sense and non-sense strands of the gene. These DNA fragments are then annealed, ligated and cloned.

Alternatively, amplification techniques can be used with precise primers to amplify a specific subsequence of the target DNA sequence encoded by the nucleic acid. The specific subsequence is then ligated into a vector.

III. First and Second Control Templates

As described above, the first control template (IC1) is a nucleic acid comprising hybridization sequences for a first control probe (HP2) flanked by target primers (P1 and P2). The second control template (IC2) is a nucleic acid comprising hybridization sequences for the target probe (HP1) and the second control probe (HP3) flanked by hybridization sequences for second control primers (P3 and P4). In some embodiments, both control templates are comprised in a single polynucleotide molecule. Alternatively, the control template can be added to the reaction mixture as separate molecules. Amplification of the first (IC1) and second (IC2) control templates provides different information about the amplification reaction. No amplification from the first control (IC1) suggests that the basic amplification reagents (enzyme, inhibitor-free solution, primers, reaction temperatures, etc.) were defective. Amplification and probe binding to the second control (IC2) provides information on the binding ability of the target probe.

The second control (IC2) provides the most information when the concentration of binding target probe (HP1) is compared to the concentration of second control probe (HP3). In the absence of the target template (T), target probe (HP1) and second control probe (HP3) should bind equal quantities of DNA. See, Table 1. If, however, the target probe is defective, then the target probe (HP1) will bind less or no DNA whereas the second control probe (HP2) should bind all of its amplified hybridization sequences. On the other hand, if the target template (T) is present and amplified, then more target probe (HP1) will bind its hybridization sequence and more target signal will be produced relative to the second control probe (HP3).

Typically, at the beginning of an amplification reaction, at least one of the first control template (IC1) and the second control template (IC2) are at concentrations higher than the target template (T). This is useful, for instance, to insure that at least one control reaction can be detected, thereby validating at least some reaction components. For example, in a preferred embodiment, the first and second control templates (IC1 and IC2) are in at least 1 to 200 copies per reaction. In a more preferred embodiment, the concentration of the first and second control templates (IC1 and IC2) is at least 5 to 100 copies per reaction. In a particularly preferred embodiment, the first and second control templates (IC1 and IC2) are at a concentration of about 10 or about 50 copies per reaction.

Moreover, in some embodiments, the concentration of the target probe (HP1), the first control probe (HP2) and the second control probe (HP3) are not the same. Similarly, in some embodiments, the concentration of target primers (P1 and P2) and the concentration of the control primers (P3 and P4) are different. Those of skill in the art will recognize that relative concentrations of different primer pairs and probes can be optimized depending on the specific reactions to be performed.

The first (IC1) and the second (IC2) control templates are preferably approximately the same length as the target template (T). Thus the time for the polymerase to make one copy of the templates will be the same, regardless of which template, target or control, is amplified.

IV. Amplification Reactions of the Invention

Amplification of an RNA or DNA template using reactions is well known (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences of target DNA sequences directly from mRNA, from cDNA, from genomic libraries or cDNA libraries. The reaction is preferably carried out in a thermal cycler to facilitate incubation times at desired temperatures. Degenerate oligonucleotides can be designed to amplify target DNA sequence homologs using the known sequences that encode the target DNA sequence. Restriction endonuclease sites can be incorporated into the primers. Polymerase chain reaction or other in vitro amplification methods may also be useful, for example, to clone nucleic acid sequences that code for the target DNA sequence proteins to be expressed. Genes amplified by the PCR reaction can be purified from agarose gels and cloned into an appropriate vector.

Exemplary PCR reaction conditions typically comprise either two or three step cycles. Two step cycles have a denaturation step followed by a hybridization/elongation step. Three step cycles comprise a denaturation step followed by a hybridization step followed by a separate elongation step.

Isothermic amplification reactions are also known and can be used according to the methods of the invention. Examples of isothermic amplification reactions include strand displacement amplification (SDA) (Walker, et al. *Nucleic Acids Res.* 20(7):1691-6 (1992); Walker *PCR Methods Appl* 3(1):1-6 (1993)), transcription-mediated amplification (Phyffer, et al., *J. Clin. Microbiol.* 34:834-841 (1996); Vuorinen, et al., *J. Clin. Microbiol.* 33:1856-1859 (1995)), nucleic acid sequence-based amplification (NASBA) (Compton, *Nature* 350(6313):91-2 (1991), rolling circle amplification (RCA) (Lisby, *Mol. Biotechnol.* 12(1):75-99 (1999)); Hatch et al., *Genet. Anal.* 15(2):35-40 (1999)) and branched DNA signal amplification (bDNA) (see, e.g., Iqbal et al., *Mol. Cell Probes* 13(4):315-320 (1999)). Other amplification methods known to those of skill in the art include CPR (Cycling Probe Reaction), SSR (Self-Sustained Sequence Replication), SDA (Strand Displacement Amplification), QBR (Q-Beta Replicase), Re-AMP (formerly RAMP), RCR (Repair Chain Reaction), TAS (Transcription Based Amplification System), and HCS.

A. Reaction components

Oligonucleotide Primers

The oligonucleotides that are used in the present invention as well as oligonucleotides designed to detect amplification products can be chemically synthesized, as described above. These oligonucleotides can be labeled with radioisotopes, chemiluminescent moieties, or fluorescent moieties. Such labels are useful for the characterization and detection of amplification products using the methods and compositions of the present invention.

The primer components may be present in the PCR reaction mixture at a concentration of, e.g., between 0.1 and 1.0 $\mu$M. As discussed above, the concentration of the target primers (P1 and P2) can be greater than the concentration of primers P3 and P4. For example, the P1-P2 concentration can be 0.6 $\mu$M while the concentration for P3 and P4 is 0.4 $\mu$M. The primer length can be between, e.g., 12-100 nucleotides in length and preferably have 50-60% G and C composition. In the choice of primer, it is preferable to have exactly matching bases at the 3' end of the primer but this requirement decreases to relatively insignificance at the 5' end. Preferably, the primers of the invention all have approximately the same melting temperature.

Buffer

Buffers that may be employed are borate, phosphate, carbonate, barbital, Tris, etc. based buffers. See Rose et al., U.S. Pat. No. 5,508,178. The pH of the reaction should be maintained in the range of about 4.5 to about 9.5. See U.S. Pat. No. 5,508,178. The standard buffer used in amplification reactions is a Tris based buffer between 10 and 50 mM with a pH of around 8.3 to 8.8. See Innis et al., supra.

One of skill in the art will recognize that buffer conditions should be designed to allow for the function of all reactions of interest. Thus, buffer conditions can be designed to support the amplification reaction as well as any enzymatic reactions associated with producing signals from probes. A particular reaction buffer can be tested for its ability to support various reactions by testing the reactions both individually and in combination.

Salt Concentration

The concentration of salt present in the reaction can affect the ability of primers to anneal to the target nucleic acid. See Innis et al. Potassium chloride is added up to a concentration of about 50 mM to the reaction mixture to promote primer annealing. Sodium chloride can also be added to promote primer annealing. See Innis et al.

Magnesium Ion Concentration

The concentration of magnesium ion in the reaction can be critical to amplifying the desired sequence(s). See Innis et al. Primer annealing, strand denaturation, amplification specificity, primer-dimer formation, and enzyme activity are all examples of parameters that are affected by magnesium concentration. See Innis et al. Amplification reactions should contain about a 0.5 to 2.5 mM magnesium concentration excess over the concentration of dNTPs. The presence of magnesium chelators in the reaction can affect the optimal magnesium concentration. A series of amplification reactions can be carried out over a range of magnesium concentrations to determine the optimal magnesium concentration. The optimal magnesium concentration can vary depending on the nature of the target nucleic acid(s) and the primers being used, among other parameters.

Deoxynucleotide Triphosphate Concentration

Deoxynucleotide triphosphates (dNTPs) is added to the reaction to a final concentration of about 20 $\mu$M to about 300 $\mu$M. Each of the four dNTPs (G, A, C, T) should be present at equivalent concentrations. See Innis et al.

Nucleic Acid Polymerase

A variety of DNA dependent polymerases are commercially available that will function using the methods and compositions of the present invention. For example, Taq DNA Polymerase may be used to amplify target DNA sequences. The PCR assay may be carried out using as an enzyme component a source of thermostable DNA polymerase suitably comprising Taq DNA polymerase which may be the native enzyme purified from *Thermus aquaticus* and/or a genetically engineered form of the enzyme. Other commercially available polymerase enzymes include, e.g., Taq polymerases marketed by Promega or Pharmacia. Other examples of thermostable DNA polymerases that could be used in the invention include DNA polymerases obtained from, e.g., Thermus and Pyrococcus species. Concentration ranges of the polymerase may range from 1-5 units per reaction mixture. The reaction mixture is typically between 20 and 100 $\mu$l.

In some embodiments, a "hot start" polymerase can be used to prevent extension of mispriming events as the temperature of a reaction initially increases. Hot starts are particularly useful in the context of multiplex PCR. Hot start polymerases can have, for example, heat labile adducts requiring a heat activation step (typically 95° C. for approximately 10-15 minutes) or can have an antibody associated with the polymerase to prevent activation.

Other Agents

Assorted other agents are sometime added to the reaction to achieve the desired results. For example, DMSO can be added to the reaction, but is reported to inhibit the activity of Taq DNA Polymerase. Nevertheless, DMSO has been recommended for the amplification of multiple target sequences in the same reaction. See Innis et al. Stabilizing agents such as gelatin, bovine serum albumin, and non-ionic detergents (e.g. Tween-20) are commonly added to amplification reactions. See Innis et B. Amplification of Multiple Target DNA Sequences The methods of the invention can be used in traditional multiplex reactions. Multiplex PCR results in the amplification of multiple polynucleotide fragments in the same reaction. See, e.g., PCR PRIMER, A LABORATORY MANUAL (Dieffenbach, ed. 1995) Cold Spring Harbor Press, pages 157-171. For instance, different target templates can be added and amplified in parallel in the same reaction vessel. Those of skill in the art will recognize that a reaction with a second (or more) target polynucleotide sequence can be monitored according to the methods of the invention by adding corresponding first and second control reactions. Thus the quality of traditional multiplex reactions (i.e., the accumulation of amplified product) can be monitored according to the methods of the invention.

The concentration of the magnesium salt in the reaction mixture can be important when trying to copy different target DNA sequences. Thus, some variation of the concentration of the magnesium salt, e.g., magnesium chloride, may be required to optimize the reaction to amplify the target nucleic acid sequences of interest. One of skill can vary the concentration of magnesium salt or ion present in the reaction mixture to arrive at the proper conditions for amplification.

V. Probes

Probes of the invention are capable of hybridizing to a particular polynucleotide sequence. Thus probes of the invention can comprise a polynucleotide sequence that is complementary to the sequence to be detected. In some embodiments, the probe also comprises a fluorophore or enzyme, as described below, which allows for the detection of the binding of the probe to its complement.

A target probe is a probe that binds to the target sequence. Thus, by quantifying binding of the target probe to its complement, the amount of amplified target sequence can be quantified. Similarly, the first and second control probes comprise polynucleotides that are capable of binding their respective control templates. As described below, the first and second control probes can also comprise a fluorophore or enzyme useful for detection of the bound probe.

Probe concentration should be sufficient to bind to the amount of target or control sequences that are amplified so as to provide an accurate assessment of the quantity of amplified sequence. Those of skill in the art will recognize that the amount of concentration of probe will vary according to the binding affinity of the probe as well as the quantity of sequence to be bound. Typical probe concentrations will range from 0.01 $\mu$M to 0.5 $\mu$M. As described above, in some embodiments, the relative amounts of one probe relative to another can be set to better differentiate the probe signals. For example, the concentration of the first control probe can be lower than the concentration of the target and second control probe to better distinguish that signal produced by the target probe.

VI. Quantification of Probe Binding

Binding of probe to its hybridization sequence allows the user to quantify the accumulation of a particular sequence without necessarily removing the contents from the reactivation vessel. In general, any type of label that allows for the detection and differentiation of different probes can be used according to the methods of the invention.

Accumulation of amplified product can be quantified by any method known to those in the art. For instance, fluorescence from a probe can be detected by measurement of light at a particular frequency. Similarly, the accumulation of various chemical products created via an enzymatic reaction linked to the probe can be measured, for instance, by measuring absorbance of light at a particular wavelength. In other embodiments, amplification reactions can be quantified directly by blotting them onto a solid support and hybridizing with a radioactive nucleic acid probe. Once unbound probe is washed away, the amount of probe can be quantified by measuring radioactivity as is known to those of skill in the art. Other variations of this technique employ the use of chemiluminescence to detect hybridization events.

Measurement of amplification products can be performed after the reaction has been completed or can be measured in "real time" (i.e., continuously). If measurement of accumulated amplified product is performed after amplification is complete, then detection reagents (e.g. probes) can be added after the amplification reaction. Alternatively, probes can be added to the reaction prior or during the amplification reaction, thus allowing for measurement of the amplified products either after completion of amplification or in real time. Real time measurements are preferred because they allow for measurement at any given cycle of the reaction and thus provide more information about accumulation of products throughout the reaction. For measurement of amplification product in real time, the use of fluorescent probes is preferred.

For instance, in a preferred embodiment, at least three different fluorophores, which fluoresce at three distinct wavelengths, are used. In this embodiment, each fluorophore is attached to each of the three different probes (e.g., target probe, first control probe and second control probe). Preferably probes based on TaqMan®, molecular beacon or FRET technology, as discussed below, are used in accordance with the invention. One of skill will recognize that a large number of different fluorophores can be used. Some fluorophores useful in the methods and composition of the invention include: fluoroscein, fluoroscein isothiocyanate (FITC), carboxy tetrachloro fluorescein (TET), NHS-fluoroscein, 5 and/or 6-carboxy fluorescein (FAM), 5- (or 6-) iodoacetamidofluoroscein, 5-{[2(and 3)-5-(Acetylmercapto)-succinyl]amino} fluoroscein (SAMSA-fluoroscein), and other fluorscein derivatives, rhodamine, Lissamine rhodamine B sulfonyl chloride, Texas red sulfonyl chloride, 5 and/or 6 carboxy rhodamine (ROX) and other rhodamine derivatives, coumarin, 7-amino-methyl-coumarin, 7-Amino-4-methylcoumarin-3-acetic acid (AMCA), and other coumarin derivatives, BODIPY™ fluorophores, Cascade Blue™ fluorophores such as 8-methoxypyrene-1,3,6-trisulfonic acid trisodium salt, Lucifer yellow fluorophores such as 3,6-Disulfonate-4-amino-naphthalimide, phycobiliproteins derivatives, Alexa fluor dyes (available from Molecular Probes, Eugene, Oreg.) and other fluorophores known to those of skill in the art. For a general listing of useful fluorophores, see Hermanson, G. T., BIOCONJUGATE TECHNIQUES (Academic Press, San Diego, 1996). Thus, each probe will fluoresce at a different wavelength and can be individually detected without interference from the other probes.

A. Fluorescence Resonance Energy Transfer

Methods employing the technique of fluorescence resonance energy transfer (FRET) can be employed using the methods and compositions of the present invention. FRET is a distance-dependent interaction between a donor and acceptor molecule. The donor and acceptor molecules are fluorophores. If the fluorophores have excitation and emission spectra that overlap, then in close proximity (typically around 10-100 angstroms) the excitation of the donor fluorophore is transferred to the acceptor fluorophore. As a result, the lifetime of the donor molecule is decreased and its fluorescence is quenched, while the fluorescence intensity of the acceptor molecule is enhanced and depolarized. When the excited-state energy of the donor is transferred to a non-fluorophore acceptor, the fluorescence of the donor is quenched without subsequent emission of fluorescence by the acceptor. In this case, the acceptor functions as a quenching reagent.

Hairpin FRET Assay

In one particular method employing FRET, fluorescent energy transfer labels are incorporated into a PCR primer that can adopt a hairpin structure. See Nazarenko et al., U.S. Pat. No. 5,866,336; Nadeau et al., U.S. Pat. No. 5,958,700; Tyagi et al., U.S. Pat. No. 5,925,517. The PCR primers can be designed in such a manner that only when the primer adopts a linear structure, i.e., is incorporated into a PCR product, is a fluorescent signal generated. See Nazarenko et al., U.S. Pat. No. 5,866,336; Nadeau et al., U.S. Pat. No. 5,958,700.

In accordance with the method of U.S. Pat. No. 5,866,336, FRET pairs can be incorporated into the primers of the present invention or into signal oligonucleotides that can be added to the reaction mix, to afford a method of detecting the incorporation of the primer into a polymerization product. The primers of the present invention or the oligonucleotides are able to adopt an intramolecularly base-paired structure (e.g., a hairpin structure). The signal oligonucleotide or the primers of the present invention are modified with two fluorescent dye moieties that form a donor/acceptor dye pair. For example, the donor dye moiety can be fluorescein or a fluorescein derivative and the acceptor can be DABCYL. The two dyes are positioned on the labeled oligonucleotide such that they are in close spatial proximity (typically around 10-100 angstroms) in the base-paired, folded secondary structure. If the dyes are in close spatial proximity then the donor fluorescence is quenched by the acceptor dye.

The hairpin primer has a quencher on its 5' terminal nucleotide, and contains a donor fluorophore on the opposite strand of its duplex, the fluorophore and quencher being a FRET pair. In the first cycle of PCR, both primers will hybridize to the respective target strands and will be extended by DNA polymerase. In the second cycle the extended product from the reverse primer will become a template for the forward primer and extended product from the forward primer will become a template for the reverse primer. When the forward primer is extended to the 5' end of the hairpin structure, either of two things can happen, depending on the DNA polymerase used: either the 5'-3' exonuclease activity of the DNA polymerase will hydrolyze the 5' nucleotides with quencher, and/or DNA polymerase will displace the 5'-end of the hairpin and copy the template. In both cases, the quencher and the fluorophore will be separated from each other and a signal will be generated.

In practice, it has been found that probes such as molecular beacons, which contain different flourophores, can be used to distinguish small differences in a target sequence (S. Tyagi et al. *Nature Biotechnology* 14, 303 (1996)), and the quantity of a target sequence (S. Tyagi et al. *Nature Biotechnology* 16, 49 (1998)).

B. TaqMan Assay

The amplification products can also be detected in solution according to the methods of the invention using a fluorogenic 5' nuclease assay—The TaqMan assay. See Holland et al., (1991) *Proc. Natl. Acad. Sci., U.S.A.* 88: 7276-7280; Livak et al. U.S. Pat. Nos. 5,538,848, 5,723,591, and 5,876,930. The TaqMan probe is designed to hybridize to a sequence within the desired PCR product. The 5' end of the TaqMan probe contains a fluorescent reporter dye. The 3' end of the probe is blocked to prevent probe extension and contains a dye that will quench the fluorescence of the 5' fluorophore. During subsequent amplification, the 5' fluorescent label is cleaved off if a polymerase with 5' exonuclease activity is present in the reaction. The excising of the 5' fluorophore results in an increase in fluorescence which can be detected.

A TaqMan probe can be used in conjunction with the present invention. For example, a probe that is labeled with an appropriate donor/quencher pair and is complementary to a portion of the target nucleic acid sequence between where the target-specific primers bind, can function in the TaqMan assay.

C. Enzymatic Reaction

A variety of enzymatic reactions are also known which can be used to detect the probes of the reaction. For example, enzymes useful in providing a detectable product for the probes of the invention include horse radish peroxidase (HRP) (see, e.g., Ausubel et al. Chapter 9), alkaline phosphatase (AP) (see, e.g., Ausubel et al. Chapter 14), urease (see, e.g., Ausubel et al. Chapter 11), β-galactosidase (see, e.g., Ausubel et al. Chapter 9), β-glucuronidase (see, e.g., Ausubel et al Chapter 9) and α-helicase (see, e.g., Eggleston, A. K., et al., *Nucleic Acids Res.* 24(7):1179-89 (1996)). The accumulation of various chemical products created via an enzymatic reaction linked to the probe can be measured, for instance, by measuring absorbance of light of the enzymatic product at a particular wavelength.

D. Hybridization

In other embodiments of the invention, amplification reactions can be quantified directly by blotting them onto a solid support (e.g., nitrocellulose) and hybridizing with a radioactive nucleic acid probe. See, e.g. Sambrook et al., supra; and Ausubel et al., supra. Once unbound probe is washed away, the amount of probe can be quantified by measuring radioactivity as is known to those of skill in the art. Other variations of this technique employ the use of chemiluminescence to detect hybridization probes.

VII. Kits and Solutions of the Invention

The invention also provides kits and solutions for carrying out the amplification methods of the invention. For example, the invention provides kits that include one or more reaction vessels that have aliquots of some or all of the reaction components of the invention in them. Aliquots can be in liquid or dried form. Reaction vessels can include sample processing cartridges or other vessels that allow for the containment, processing and/or amplification of samples in the same vessel. Such kits allow ready detection of amplification products of the invention into standard or portable amplification devices. The kits can also include written instructions for the use of the kit to amplify and control for amplification of a target sample.

Kits can include, for instance, (1) a target probe, a first control probe and a second control probe, (2) a first 5' primer and a first 3' primer, and (3) a first control template. The first control template can comprise a hybridization site for the first 5' primer, the first 3' primer and the first control probe. The kit can also include a second 5' primer, a second 3' primer and a second control template. The second control template can comprise a hybridization site for the second 5' primer, the second 3' primer, the target probe and the second control probe. The kit's target probe, first control probe and second control probe comprise a fluorophore, including a quenching agent. In addition, the kit can include nucleotides (A, C, G, T) and a DNA polymerase.

In presently preferred embodiments, the kits comprise vessels such as sample processing cartridges useful for rapid amplification of a sample as described in Belgrader, P., et al., *Biosensors and Bioelectronics* 14:849-852 (2000); Belgrader, P., et al., *Science*, 284:449-450 (1999); and Northrup, M. A., et al. "A New Generation of PCR Instruments and Nucleic Acid Concentration Systems" in PCR PROTOCOLS (Sninsky, J. J. et al (eds.)) Academic, San Diego, Chapter 8 (1998)).

VIII. Quantitative Amplification Reactions

The methods of the invention are well suited for use in quantitative amplification reactions such as quantitative PCR. Quantitative amplification refers to methods for detecting the quantity of nucleic acid template in a sample. The methods generally involve comparing the rate of amplification of a sample (as measured in number of reaction cycles) with amplification of a known amount of template, i.e. the concentration of a positive control or competitor sequence. See, e.g., Orlando et al., *Clin. Chem. Lab. Med.* 36(5):255-69 (1998); Gililand, G. et al., *Proc. Natl. Acad. Sci. USA*, 87:2725-2729 (1990). Quantification of the amplification reaction is performed by comparing the final concentration of the target with known amounts of the competitor. The reactions of the invention include internal positive controls that can act as competitors for quantification. Therefore, all of the data necessary for quantifying the products of an amplification reaction can be obtained from a single reaction of the invention. Moreover, quantitative amplification reactions can be measured at real time according to the methods of the invention.

Studies have shown that initial copy number can be quantified during real-time PCR analysis based on threshold cycle (Ct). See, Higuchi, R., et al. *Biotechnology* 11:1026-1030 (1993). Ct is defined as the cycle at which fluorescence is determined to be statistically significant above background. The threshold cycle is inversely proportional to the log of the initial copy number. The more template that is present to begin with, the fewer the number of cycles it takes to get to a point where the fluorescent signal is detectable above background. Quantitative information based on threshold cycle can be more accurate than information based on endpoint determinations because it is based on a measurement taken during the exponential phase of PCR amplification when the PCR efficiency has yet to be influenced by limiting reagents, small differences in reaction components, or cycling conditions.

Table 1 demonstrates how the cycle threshold values are useful to determine the integrity of a particular reaction. The table provides hypothetical Ct values depending on different reaction scenarios.

TABLE 1

Interpretation of Real-Time PCR Results Based on Cycle Threshold Values of Hybridization Probes 1, 2, and 3

| Sample | HP1: (target and IC2) | HP2: (IC1) | HP3: (IC2) | Test Result |
|---|---|---|---|---|
| Negative, non-inhibiting | Same as HP3. Ct is less than or equal to Y | Ct is less than or equal to X | Same as HP1. Ct is less than or equal to Y | Negative |
| High positive, non-inhibiting | Ct is significantly less than HP3 by a factor of z | No Ct value or Ct is less than or equal to X | No cycle threshold or Ct is greater than HP1 and less than or equal to Y | Positive |
| Low positive, non-inhibiting | Ct is less than HP3 | Ct is less than or equal to X | Ct is greater than HP1 and less than or equal to Y | Positive |
| Reagent degradation | No Ct value | No Ct value | No Ct value | Invalid |
| Negative, inhibitors present in sample | No Ct value or Ct is equal to HP3 | No Ct value or Ct is greater than X or low fluorescent endpoint value | No Ct values or Ct is greater than Y or low fluorescent endpoint value | Invalid |

TABLE 1-continued

Interpretation of Real-Time PCR Results Based on Cycle Threshold Values of Hybridization Probes 1, 2, and 3

| Sample | HP1: (target and IC2) | HP2: (IC1) | HP3: (IC2) | Test Result |
|---|---|---|---|---|
| Positive, inhibitors present in sample | Ct is less than HP3 | Ct is greater than X or low fluorescent endpoint value | Ct is greater than Y or low fluorescent endpoint value | Positive result; unable to quantitate due to inhibitors | z = factor defining separation between HP1 and HP3 Ct values
X = maximum Ct value for a valid result for Probe 2 (IC1)
Y = maximum Ct value for a valid result for Probe 3 (IC2)

EXAMPLE

A method is described whereby the addition of two internal controls (IC) provide assurance that clinical specimens are successfully amplified and detected in a real-time assay format. The first IC is used to monitor the integrity of the amplification mix, including the primers, dNTPs, and polymerase. The second IC controls for the integrity of the target-specific hybridization probe. The value of the two internal controls is that obtaining a positive signal from both demonstrates successful amplification, thereby validating a true negative result for the target specimen.

Materials and Methods

A 10 μL sample of processed specimen is added to 15 μL of master mix containing IC1 at 100 copies, IC2 at 10 copies, 0.6 μM each primer 1 and primer 2, 0.4 μM each primer 3 and primer 4, 200 μM each dNTP, 0.4 μM FAM-labeled target- and IC2-specific hybridization probe (HP1), 0.2 μM TET-labeled IC1-specific hybridization probe (HP2), 0.2 μM ROX-labeled IC2 hybridization probe (HP3), and 1.25 units of a hot-start polymerase with 5' to 3' nuclease activity. All reactions are carried out in a 1× amplification buffer: 10 mM Tris-HCl, pH 8.0, 50 mM KCl, and 3.5 mM $MgCl_2$. Samples are cycled in the Cepheid Smart Cycler® System using the following thermal cycling parameters: 95° C. for 90 seconds (initial denaturation) and then 40 cycles of 95° C. for 15 seconds and 60° C. for 30 seconds.

Interpretation of Results

The value "X" is defined as the maximum cycle threshold (Ct) value for a valid result for HP2. The value "Y" is defined as the maximum Ct value for a valid result for HP3. Factor "z" represents the difference between the actual measurements if HP1 (as measured by FAM) and HP3 (as measured by ROX) Ct values.

Specimens yielding a FAM Ct value (target and IC2) a factor "z" less than Y are interpreted as positive, regardless of IC1 (TET) and IC2 (ROX) results. See, Table 1. Specimens yielding a FAM Ct value less than Y are interpreted as positive, if the Ct value of IC1 (TET) is equal to or less than X and the Ct value of IC2 (ROX) is equal to or less than Y. See, Table 1. Specimens yielding a FAM Ct value (target and IC2) equal to the Ct value of IC2 (ROX) that is equal to or less than Y, are interpreted as negative if the Ct value of IC1 (TET) is equal to or less than X. Specimens yielding no positive signals are invalid and must be repeated. Specimens yielding no FAM Ct values or FAM Ct values equal to the Ct value of IC2 (ROX) are interpreted as invalid if the Ct values for IC1 (TET) and IC2 (ROX) are greater than X and Y, respectively. See, Table 1. Specimens yielding a FAM Ct value (target and IC2) less than the Ct value of IC2 (ROX) are interpreted as positive without the ability to quantitate due to inhibitors, if the Ct value for IC1 (TET) and IC2 (ROX) are greater than X and Y, respectively, or low endpoint fluorescence values are obtained. See, Table 1.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A kit comprising:
   (a) a target probe, a first control probe and a second control probe, wherein each probe comprises a fluorophore and a quenching agent;
   (b) a first 5' primer and a first 3' primer;
   (c) a first control template, the first control template comprising a hybridization site for the first 5' primer, the first 3' primer and the first control probe; and
   (d) a second 5' primer, a second 3' primer and a second control template, the second control template comprising a hybridization site for the second 5' primer, the second 3' primer, the target probe and the second control probe.

2. The kit of claim 1, wherein the kit further comprises nucleotides and a DNA polymerase.

3. The kit of claim 1, wherein the kit further comprises a sample processing cartridge.

4. A solution comprising:
   (a) a target probe, a first control probe and a second control probe;
   (b) a first 5' primer and a first 3' primer;
   (c) a first control template, the first control template comprising a hybridization site for the first 5' primer, the first 3' primer and the first control probe; and
   (d) a second 5' primer, a second 3' primer and a second control template, the second control template comprising a hybridization site for the second 5' primer, the second 3' primer, the target probe and the second control probe.

5. A solution comprising:
   (a) a target probe, a first control probe and a second control probe, wherein each probe comprises a fluorophore and a quenching agent;
   (b) a first 5' primer and a first 3' primer;

(c) a first control template, the first control template comprising a hybridization site for the first 5' primer, the first 3' primer and the first control probe; and (d) a second 5' primer, a second 3' primer and a second control template, the second control template comprising a hybridization site for the second 5' primer, the second 3' primer, the target probe and the second control probe.

* * * * *

UNITED STATES PATENT AND TRADEMARK OFFICE
CERTIFICATE OF CORRECTION

PATENT NO. : 6,534,645 B2  Page 1 of 1
DATED : March 18, 2003
INVENTOR(S) : William A. McMillan It is certified that error appears in the above-identified patent and that said Letters Patent is hereby corrected as shown below:

Column 18,
Line 52, after the word "probe"; insert therefor -- wherein each probe comprises a fluorophore and a quenching agent; --
Lines 62-66, Claim 5 is a duplicate of claim 4. Please delete all text and insert therefor -- The solution of claim 4, wherein the solution further comprises nucleotides and a DNA polymerase. --

Signed and Sealed this

Twenty-third Day of September, 2003

JAMES E. ROGAN
*Director of the United States Patent and Trademark Office*